United States Patent [19]

Weber et al.

[11] 4,431,732
[45] Feb. 14, 1984

[54] PROCESS FOR THE PREPARATION OF 11β,21-DIHYDROXY-2'-METHYL-5'βH-1,4-PREGNADIENO(16,17-D)-OXAZOLE-3,20-DIONE

[75] Inventors: Alfred Weber; Mario Kennecke; Rudolf Müller, all of Berlin, Fed. Rep. of Germany

[73] Assignee: Schering Aktiengesellschaft, Berlin and Bergkamen, Fed. Rep. of Germany

[21] Appl. No.: 334,025

[22] Filed: Dec. 23, 1981

[30] Foreign Application Priority Data

Dec. 23, 1980 [DE] Fed. Rep. of Germany ....... 3049401

[51] Int. Cl.³ .............................................. C12P 33/02
[52] U.S. Cl. ....................................................... 435/61
[58] Field of Search ..................................... 435/61, 55

[56] References Cited

U.S. PATENT DOCUMENTS

| | | | |
|---|---|---|---|
| 2,981,659 | 4/1961 | Fonken et al. | 435/53 |
| 3,274,182 | 9/1966 | Dryden et al. | 435/53 |
| 3,560,486 | 2/1971 | Marx et al. | 435/53 |
| 3,684,656 | 8/1972 | van der Waard | 435/55 |
| 3,718,673 | 2/1973 | Ripka | 435/61 |
| 4,101,378 | 7/1978 | Nishikawa et al. | 435/61 |
| 4,246,346 | 1/1981 | Larsson et al. | 435/61 |

FOREIGN PATENT DOCUMENTS 1693041 7/1971 Fed. Rep. of Germany .

OTHER PUBLICATIONS

Charney, Microbial Transformations of Steroids, Academic Press, New York, 1967, p. 356 ff.

Primary Examiner—Alvin E. Tanenholtz
Attorney, Agent, or Firm—Millen & White

[57] ABSTRACT

A process for preparing 11β,21-dihydroxy-2'-methyl-5'βH-1,4-pregnadieno(16,17-d)-oxazole-3,20-dione, comprises fermenting 11β,21-dihydroxy-2'-methyl-5'βH-4-pregneno (16,17-d)-oxazole-3,20-dione with a living culture of *Arthrobacter simplex*.

5 Claims, No Drawings

PROCESS FOR THE PREPARATION OF 11β,21-DIHYDROXY-2'-METHYL-5'βH-1,4-PREGNADIENO(16,17-D)-OXAZOLE-3,20-DIONE

BACKGROUND OF THE INVENTION

The present invention relates to a microbiological process for preparing 11β,21-dihydroxy-2'-methyl-5'βH-1,4-pregnadieno(16,17-d)-oxazole-3,20-dione, which is useful as a well known antiinflammatory active corticoide.

The microbiological $\Delta^1$-dehydrogenation of 11β,21-dihydroxy-2'-methyl-5'βH-4-pregneno(16,17-d)-oxazole-3,20-dione cannot be conducted as readily as that of other steroids. This has been determined by recent experiments. The fermentation of this compound with living cultures of conventional steroid -$\Delta^1$-dehydrogenating agents, such as *Bacillus lentus* ATCC 13 805, *Bacillus sphaericus* ATCC 7054, ATCC 7055, and ATCC 12 488, *Bacillus subtilis* NRRL B 558, as well as *Norcardia corallina* ATCC 4273 and 4275 produces unsatisfactory results. Hardly any conversion of the substrate is observed, and the substrate is greatly metabolized.

SUMMARY OF THE INVENTION

It is an object of this invention to provide a method for $\Delta^1$-dehydrogenating the subject compound to produce 11β,21-dihydroxy-2'-methyl-5'βH-1,4-pregnadieno-(16,17-d)-oxazole-3,20-dione.

Upon further study of the specification and appended claims, further objects and advantages of this invention will become apparent to those skilled in the art.

These objects have been achieved by the discovery that the microbiological $\Delta^1$-dehydrogenation of 11β,21-dihydroxy-2'-methyl-5'βH-4-pregneno(16,17-d)-oxazole-3,20-dione can be conducted with satisfactory results by using a microorganism of the species *Arthrobacter simplex*. Suitable *Arthrobacter simplex* strains include, for example, the strains IFO (3530), ATCC 13 260, and especially ATCC 6946.

DETAILED DISCUSSION

It has long been known that *Arthrobacter simplex*, previously called *Corynebacterium simplex*, possesses activity for $\Delta^1$-dehydrogenation of steroids. This microorganism is frequently used in industrial applications, since it has the advantage over most of the aforementioned steroid $\Delta^1$-dehydrogenating microorganisms that the reaction using it proceeds substantially faster than with those microorganisms; however, on the other hand, *Arthrobacter simplex* does have two disadvantages. This microorganism frequently tends to metabolize steroids during a prolonged fermentation period. This can lead to not inconsiderable losses in yield of the desired product. Moreover, this microorganism frequently tends to stop the reaction when 1–3% of starting steroid is still present in the culture broth. This makes it often quite difficult to obtain the products of the process in a purity indispensible for use in pharmaceutical agents. The two aforementioned disadvantages are also observed in the fermentation of 11β,21-dihydroxy-2'-methyl-5'βH-pregneno(16,17-d)-oxazole-3,20-dione.

Surprisingly, it has now been found that even these disadvantages can be avoided by conducting the $\Delta^1$-dehydrogenation with *Arthrobacter simplex* in the presence of 0.04 g to 0.12 g of cobalt(II) ions per liter of culture broth. A smaller concentration of cobalt ions does not provide any appreciable effect; a higher concentration of cobalt(II) ions has an inhibitory effect. Suitable cobalt(II)-ion-yielding agents include water-soluble cobalt salts, e.g., $CoCl_2$, $Co(NO_3)_2$, $CoSO_4$, or $CoSO_4.7H_2O$. The anions of these salts are without importance for the feasibility of the process since the cobalt(II) salts are dissociated in the culture medium.

Otherwise, the process of this invention is conducted under conditions conventionally employed for the $\Delta^1$-dehydrogenation of steroids with microorganisms of the species *Arthrobacter simplex* formerly named *Cornebacterium simplex* (see e.g. W. Charney and H. L. Herzog: Microbial Transformations of Steroids Academic Press, New York, 1967, pages 356 ff whose disclosures are incorporated by reference herein.)

Under the culturing conditions usually employed for this microorganism, a submerged culture is grown in a suitable nutrient medium under aeration. Then, the substrate (dissolved in a suitable solvent or preferably in emulsified form) is added to the cultures and the mixture is fermented until a maximum substrate conversion has been achieved.

Suitable substrate solvents include, for example, methanol, ethanol, glycol monomethyl ether, dimethylformamide, or dimethyl sulfoxide. An especially suitable solvent is hexamethylphosphoric triamide. Typically, the substrate is added to the broth as a 2–7% solution by weight. Emulsification of the substrate can be effected, for example, by introducing this substrate, in micronized form or dissolved in a water-miscible solvent (e.g. methanol, ethanol, acetone, glycol monomethyl ether, dimethylformamide, or dimethyl sulfoxide) through nozzles under strong turbulence into (preferably demineralized) water containing the usual emulsifiers. Suitable emulsifiers include nonionic emulsifiers, e.g. ethylene oxide adducts or fatty acid esters of polyglycols. Suitable emulsifiers which can be cited as examples are the commercial surfactants "Tegin", "Tagat", "Tween", and "Span".

The optimum substrate concentration, time of adding the substrate, and duration of fermentation, as usual, are dependent on the type of microorganism employed. These variables must be determined, as generally required in microbiological steroid conversions, in each individual case by preliminary experiments well known to those skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example, all temperatures are set forth uncorrected in degrees Celsius; unless otherwise indicated, all parts and percentages are by weight.

The protein hydrolysate utilized in the following example was produced from ground feathers according to the directions in Organic Synthesis, Col. Vol. I, p. 194; but after hydrolysis had taken place, the product was neutralized with ammonia and filtered under sterile conditions. The resultant filtrate was employed as the "protein hydrolysate" without further purification.

EXAMPLE (a) A 2-liter Erlenmeyer flask charged with 1 liter of a sterile nutrient solution containing 0.5% cornsteep liquor
0.05% glucose monohydrate
0.1% yeast extract
adjusted to pH 7.0 is inoculated with a supernatant broth of a dry culture of Arthrobacter simplex ATCC 6946 and shaken at 30° C. for 72 hours at 180 rpm.

(b) A 50-liter fermentor with 30 l of sterile nutrient solution containing 0.5% cornsteep liquor
0.05% glucose monohydrate
0.1% yeast extract
4 ml silicone SH
4 ml "Pluronic"
adjusted to pH 7.0 is inoculated with 1 liter of *Arthrobacter simplex* incubation culture, and this preliminary culture is incubated at 30° C. under aeration (2 m³ per hour) and agitation (220 rpm) for 24 hours.

(c) 15 g of 11β,21-dihydroxy-2'-methyl-5'βH-4-pregneno(16,17-d)-oxazole-3,20-dione having a melting point of 114°/118°–130° C. is dissolved in 300 ml of hexamethylphosphoric triamide and then filtered under sterile conditions.

(d) 12 g of $CoSO_4.7H_2O$ and 12 g of $(NH_4)_2SO_4$ are dissolved in 500 ml of water, adjusted to pH 6.5, and sterilized.

(e) A 50-liter fermentor is charged with 30 l of a sterile nutrient solution containing 0.5% cornsteep liquor
0.05% glucose monohydrate
0.3% "protein hydrolysate"
4 ml silicone SH
4 ml "Pluronic"
adjusted to pH 7.0 inoculated with 3 l of Arthrobacter simplex preliminary culture, and incubated under aeration (2 m³ per hour) and agitation (220 rpm) for 6 hours at 30° C. Then the sterile 11β,21-dihydroxy-2'-methyl-5'βH-4-pregneno(16,17-d)-oxazole-3,20-dione solution prepared in paragraph (c) and the additives produced in paragraph (d) are added thereto. Thereafter the fermentation is continued for another 20 hours.

After fermentation has taken place, the culture broth, stabilized with 5 l of ethylene chloride, is extracted three times with respectively 20 l of ethylene chloride, and the ethylene chloride extract is concentrated under vacuum at maximally 50° C. in a forced circulation evaporator. The product is then purified by chromatography on aluminum oxide.

Yield: 11.4 g of 11β,21-dihydroxy-2'-methyl-5'βH-1,4-pregnadieno(16,17-d)-oxazole-3,20-dione, mp 210°/212°–220° C.

What is claimed is:

1. A process for preparing 11β,21-dihydroxy-2'-methyl-5'βH-1,4-pregnadieno(16,17-d)-oxazole-3,20-dione consisting essentially of fermenting 11β,21-dihydroxy-2'-methyl-5'βH-4-pregneno(16,17-d)-oxazole-3,20-dione with a living culture of *Arthrobacter simplex* in the presence of 0.04–0.12 g of cobalt(II) ions per liter of culture broth.

2. A process of claim 1 for preparing 11β,21-dihydroxy-2'-methyl-5'βH-1,4-pregnadieno(16,17-d)-oxazole-3,20-dione wherein the 11β,21-dihydroxy-2'-methyl-5'βH-4-pregneno(16,17-d)-oxazole-3,20-dione is added to the culture broth as a 2–7% by weight solution in hexamethylphosphoric triamide.

3. A process of claim 1 for preparing 11β,21-dihydroxy-2'-methyl-5'βH-1,4-pregnadieno(16,17-d)-oxazole-3,20-dione wherein the fermentation is conducted with a living culture of *Arthrobacter simplex* ATCC 6946.

4. A process of claim 1 wherein the fermentation is conducted with a living culture of *Arthrobacter simplex* IFO (3530) or ATCC (13,260).

5. A process of claim 1 wherein the cobalt ions are provided by addition of a water soluble Co(II) salt which is $CoCl_2$, $Co(NO_3)_2$, $CoSO_4$ or $CoSO_4.7H_2O$.

* * * * *